US00PP25901P2

(12) United States Plant Patent
Verschoor

(10) Patent No.: US PP25,901 P2
(45) Date of Patent: Sep. 15, 2015

(54) *VERONICA* PLANT NAMED 'BABY BOMB'

(50) Latin Name: ***Veronica* hybrid**
Varietal Denomination: Baby Bomb

(71) Applicant: Jan Verschoor, Haarlem (NL)

(72) Inventor: Jan Verschoor, Haarlem (NL)

(73) Assignee: A. VERSCHOOR HORTICULTURE IMPORT-EXPORT B.V., Haarlem (NL)

( * ) Notice: Subject to any disclaimer, the term of this patent is extended or adjusted under 35 U.S.C. 154(b) by 102 days.

(21) Appl. No.: 13/999,117

(22) Filed: Jan. 15, 2014

(51) Int. Cl.
*A01H 5/02* (2006.01)

(52) U.S. Cl.
USPC ..... Plt./251

(58) Field of Classification Search
USPC ..... Plt./251
See application file for complete search history.

*Primary Examiner* — Susan McCormick Ewoldt
(74) *Attorney, Agent, or Firm* — Penny J. Aguirre

(57) ABSTRACT

A new cultivar of *Veronica,* 'Baby Bomb', that is characterized by its compact, upright and strong plant habit, its flowers that are deep violet-blue in color, its freely branched plant habit forming a dense shrub-like plant, its compact and freely branched inflorescences, its long blooming habit and its low, dense shrubby habit as a mature plant.

2 Drawing Sheets

Botanical classification: *Veronica* hybrid.
Cultivar designation: 'Baby Bomb'.

BACKGROUND OF THE INVENTION

The present invention relates to a new and distinct cultivar of *Veronica,* botanically a *Veronica* of hybrid origin and will be referred to hereafter by its cultivar name, 'Baby Bomb'. 'Baby Bomb' represents a new herbaceous perennial grown for landscape use.

'Baby Bomb' was selected by the Inventor as a seedling in a seedling bed in Haarlem, The Netherlands in summer of 2010. The seedling bed had been planted with seeds collected from open pollinated plants of *Veronica* cultivar 'Blue Bomb' (U.S. Plant Pat. No. 22,509). The male parent is therefore unknown.

Asexual propagation of the new cultivar was first accomplished by softwood cuttings by the Inventor in summer of 2010 in Haarlem, The Netherlands. Asexual propagation by division and softwood cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Baby Bomb' as a unique cultivar of *Veronica.*

1. 'Baby Bomb' exhibits a compact, upright, and strong plant habit.
2. 'Baby Bomb' exhibits flowers that are deep violet-blue in color.
3. 'Baby Bomb' exhibits a freely branched plant habit forming a dense shrub-like plant.
4. 'Baby Bomb' exhibits compact and freely branched inflorescences.
5. 'Baby Bomb' exhibits a long blooming habit.
6. 'Baby Bomb' exhibits a low, dense shrubby habit as a mature plant.

The parent of 'Baby Bomb', 'Blue Bomb', differs from 'Baby Bomb' in being taller in height, in having flowers that are lighter in color, in having a more vigorous growth rate, and in having less branched, less compact inflorescences. 'Baby Bomb' can be most closely be compared to the *Veronica* cultivars 'Blue Explosion' (U.S. Plant Pat. No. 22, 497) and 'Sunny Border Blue' (not patented). Both are similar to 'Baby Bomb' in having flowers that are violet-blue in color. 'Blue Explosion' differs from 'Baby Bomb' in having less branched and less compact inflorescences, in being taller in height, in having a more vigorous growth rate, and in having foliage that is lighter green in color. 'Sunny Border Blue' differs from 'Baby Bomb' in having a less compact plant habit, in having much weaker stems, in having less branched and less compact inflorescences, and in having a shorter bloom period.

BRIEF DESCRIPTION OF THE DRAWINGS

The accompanying colored photographs illustrate the overall appearance and distinct characteristics of the new *Veronica.* The photographs were taken of nine month-old plants of 'Baby Bomb' as grown outdoors in five-gallon containers in Haarlem, The Netherlands.

The photograph in FIG. 1 provides a side view of a plant of 'Baby Bomb' in bloom.

Figure 1:
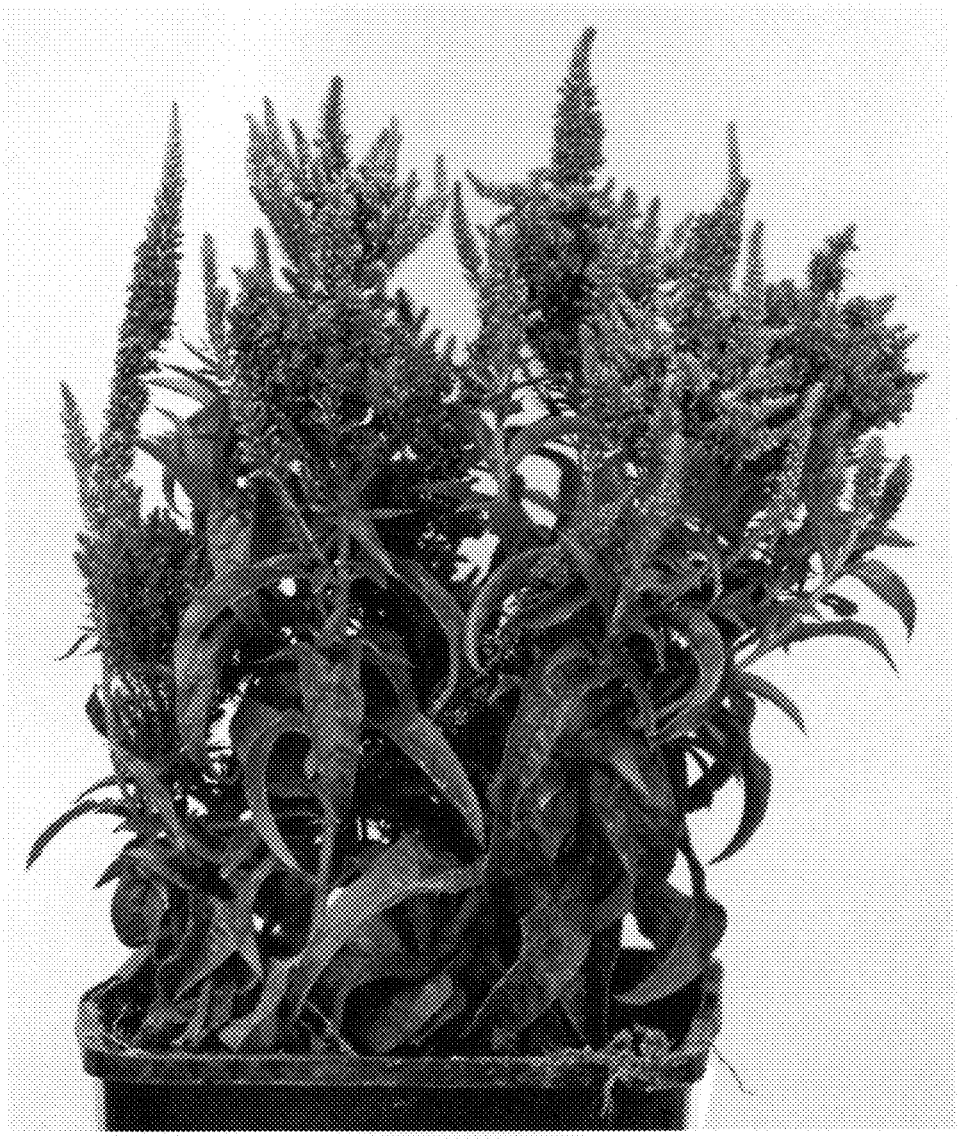
Figure 2:
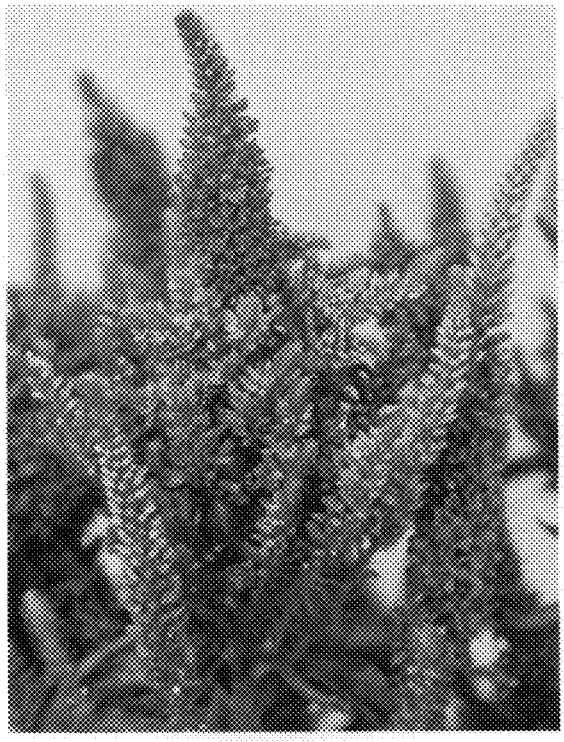

The photograph in FIG. 2 provides a close-up view of the inflorescences of 'Baby Bomb'.

Figure 3:
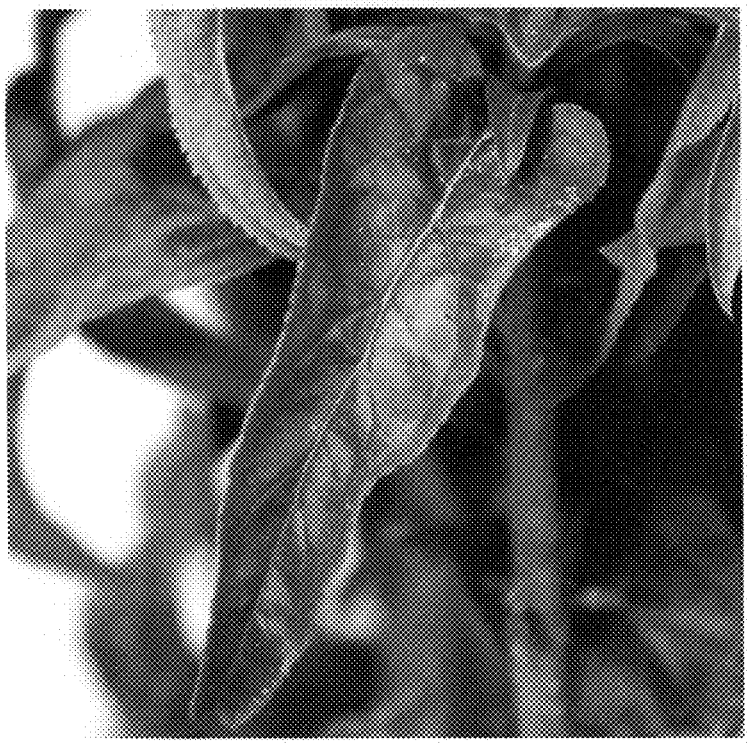

The photograph in FIG. 3 provides a close-up view of the foliage of 'Baby Bomb'.

The colors in the photograph may differ slightly from the color values cited in the detailed botanical description, which accurately describe the colors of the new *Veronica.*

DETAILED BOTANICAL DESCRIPTION

The following is a detailed description of the new cultivar as observed for a plant about 9-months in age as field grown outdoors in Haarlem, The Netherlands. The plants were grown under average day temperatures of 15° to 30° C. and average night temperatures of 6° to 18° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Continuously from June to September in The Netherlands.

*Plant type*.—Herbaceous perennial.

*Plant habit*.—Compact and upright, with strong densely branched stems, forms a low, dense shrubby habit as a mature plant.

*Height and spread*.—Reaches about 32 cm in height and 25 cm in spread.

*Hardiness*.—At least hardy in U.S.D.A. Zone 4.

*Diseases*.—Not significantly different in susceptibility or resistance than other *Veronica* varieties.

*Growth rate*.—Slow to moderate.

*Propagation*.—Division or softwood cuttings.

*Growth rate*.—Low to moderate.

Stem description:

*Shape*.—Round.

*Stem quantity*.—Average of 7 main stems.

*Stem color*.—143B to 143C.

*Stem size*.—Average of 5 mm in diameter and 13.6 cm (excluding inflorescence) in length.

*Stem surface*.—Slightly glossy and densely covered with pubescence hairs; an average of 2 mm in length and 157D in color.

*Stem aspect*.—Held at an average angle of 85° to soil level.

*Branching habit*.—Freely branching from the base.

Foliage description:

*Leaf division*.—Simple.

*Leaf arrangement*.—Opposite.

*Leaf shape*.—Narrow ovate to lanceolate, slightly to moderately curved and slightly carinate.

*Leaf size*.—An average of 7.3 cm in length and 2.7 cm in length.

*Leaf number*.—Average of 14 per branch.

*Leaf base*.—Truncate.

*Leaf apex*.—Acute.

*Leaf margin*.—Finely serrate with an average of 8 teeth per cm.

*Leaf venation*.—Pinnate, upper surface 144A in color, lower surface 145A to 145B in color.

*Leaf surface*.—Upper surface moderately glossy, lower surface matte, both surfaces moderately to densely covered with very short pubescent hairs; 157D in color, average length of hairs on upper surface is 1 mm, average length of hairs on lower surface is 2 mm.

*Leaf color*.—Young upper surface; 143A, young lower surface; color between 143B and 144A, mature upper surface; color between N137B and 147A, mature lower surface; 147B.

*Leaf attachment*.—Sessile.

Flower description:

*Inflorescence type*.—Compound terminal racemes of rotate-shaped flowers.

*Lastingness of inflorescence*.—Individual flowers last 3 to 4 days, inflorescence lasts about 10 days, blooms from bottom of raceme towards apex.

*Inflorescence size*.—Average of 15.1 cm in length and 8.3 cm in diameter.

*Flower type*.—Rotate.

*Flower number*.—Average of 4,200 per compound raceme (25,000 per plant).

*Flower fragrance*.—Faint to moderately sweet.

*Flower buds*.—Ovate in shape, about 4 mm in length and 15 mm in diameter, N88A in color.

*Flower size*.—About 6 mm in depth and 7 mm in diameter.

*Peduncles*.—Primary peduncle; 15.4 cm in length and 2 mm in diameter, held vertically, strong, and 138A to 138B in color, secondary peduncles; 6.4 cm in length and 1.5 mm in diameter, held at an average angle of 45°, strong and 138A to 138B in color.

*Pedicels*.—An average of 1 mm in length and 0.5 mm in width, held at an average angle of 45°, strong, 138A to 138B in color.

*Calyx*.—Rotate in shape, average of 25 mm in length and 2.5 mm in diameter.

*Sepals*.—4, rotate, narrow ovate in shape, base is cuneate with lower 5% fused, matte and glabrous surfaces, entire margin, acute apex, lower sepals 2.5 mm in length and 0.75 mm in width, upper sepals 1.5 mm in length and 0.75 mm in width, color of immature and mature upper surfaces 143A, color of immature and mature lower surfaces 137D.

*Petals*.—4, oblanceolate in shape, obtuse apex, lower 40% fused, entire margin, color of upper and lower surfaces when opening; N88A, color of upper and lower surfaces when fully open; N88A to N88B, up to 5 mm in length and 2 mm in width, matte and glabrous on both surfaces.

Reproductive organs:

*Gynoecium*.—1 Pistil, style is about 4.5 mm in length and 86A to 86B in color, stigma is clavate in shape and 79A in color, ovary is superior and 145A in color.

*Androecium*.—2 stamens, filament is about 5 mm in length and N88A in color, anthers are dorsifixed and elliptic in shape, about 2 mm in length and N77C in color, pollen is moderate in quantity and 4A to 4B in color.

*Fruit*.—Fruit and seed production has not been observed.

It is claimed:

1. A new and distinct cultivar of *Veronica* plant named 'Baby Bomb' as herein illustrated and described.

* * * * *